(12) United States Patent
Yankelevitz et al.

(10) Patent No.: US 7,596,401 B2
(45) Date of Patent: Sep. 29, 2009

(54) METHOD FOR EXPANDING THE DOMAIN OF IMAGING SOFTWARE IN A DIAGNOSTIC WORK-UP

(75) Inventors: David F. Yankelevitz, Brooklyn, NY (US); Anthony P. Reeves, Ithaca, NY (US); Claudia Ingrid Henschke, New York, NY (US)

(73) Assignee: Cornell Research Foundation, Inc., Ithaca, NY (US)

(*) Notice: Subject to any disclaimer, the term of this patent is extended or adjusted under 35 U.S.C. 154(b) by 502 days.

(21) Appl. No.: 11/377,031

(22) Filed: Mar. 16, 2006

(65) Prior Publication Data
US 2006/0239544 A1  Oct. 26, 2006

Related U.S. Application Data

(60) Provisional application No. 60/662,190, filed on Mar. 16, 2005.

(51) Int. Cl.
*A61B 5/00*  (2006.01)
(52) U.S. Cl. .................................. 600/407; 382/128
(58) Field of Classification Search .......... 600/407–469
See application file for complete search history.

(56) References Cited

U.S. PATENT DOCUMENTS

| | | | |
|---|---|---|---|
| 5,622,171 A * | 4/1997 | Asada et al. ............... | 600/408 |
| 5,815,591 A | 9/1998 | Roehrig et al. | |
| 5,917,929 A | 6/1999 | Marshall et al. | |
| 5,984,870 A * | 11/1999 | Giger et al. ................ | 600/443 |
| 6,014,452 A | 1/2000 | Zhang et al. | |
| 6,035,056 A | 3/2000 | Karssemeijer | |
| 6,075,879 A | 6/2000 | Roehrig et al. | |
| 6,198,838 B1 | 3/2001 | Roehrig et al. | |
| 6,263,092 B1 | 7/2001 | Roehrig et al. | |
| 6,266,453 B1 | 7/2001 | Hibbard et al. | |
| 6,301,378 B1 | 10/2001 | Karssemeijer et al. | |
| 6,404,908 B1 | 6/2002 | Schneider et al. | |
| 6,580,818 B2 | 6/2003 | Karssemeijer et al. | |
| 6,640,001 B2 | 10/2003 | Roehrig et al. | |
| 6,909,794 B2 | 6/2005 | Caspi | |
| 6,909,795 B2 | 6/2005 | Tecotzky et al. | |
| 6,909,797 B2 | 6/2005 | Romsdahl et al. | |
| 6,925,200 B2 | 8/2005 | Wood et al. | |
| 7,054,473 B1 | 5/2006 | Roehrig et al. | |

(Continued)

OTHER PUBLICATIONS

R2 Technology, Inc., What is CAD?,2004.

(Continued)

*Primary Examiner*—Long V Le
*Assistant Examiner*—Vani Gupta
(74) *Attorney, Agent, or Firm*—Citadel Patent Law; George A. Leone (57) ABSTRACT

A method for expanding the domain of imaging software in a diagnostic work-up includes the steps of:
  imaging a patient's body parts for a first condition using a first imaging technique directed to a first condition;
  acquiring known patient risk factors indicating a second condition;
  compensating for differences in accuracy between a first imaging technique directed to a first condition, and a second imaging technique directed to testing for the second condition to generate a set of measures;
  placing a range and confidence interval around the set of measures; and
  evaluating for a second condition using the set of measures and known patient risk factors.

14 Claims, 4 Drawing Sheets

U.S. PATENT DOCUMENTS

| | | |
|---|---|---|
| 2002/0159622 A1 | 10/2002 | Schneider |
| 2003/0095696 A1 | 5/2003 | Reeves |
| 2004/0101095 A1* | 5/2004 | Jing et al. .................... 378/37 |
| 2004/0184647 A1 | 9/2004 | Reeves |
| 2004/0252870 A1 | 12/2004 | Reeves |
| 2005/0013471 A1 | 1/2005 | Snoeren et al. |
| 2005/0049497 A1* | 3/2005 | Krishnan et al. ............ 600/437 |
| 2005/0163360 A1 | 7/2005 | Snoeren et al. |
| 2006/0084860 A1* | 4/2006 | Geiger et al. ............... 600/407 |
| 2006/0147099 A1 | 7/2006 | Marshall |

OTHER PUBLICATIONS

University of Virginia School of Medicine, Lines and Tubes, 1999.
National Cancer Institute, Improving Methods for Breast Cancer Detection and Diagnosis, Apr. 26, 2002.

* cited by examiner

*FIG. 4* ic work-up.

METHOD FOR EXPANDING THE DOMAIN OF IMAGING SOFTWARE IN A DIAGNOSTIC WORK-UP

CROSS-REFERENCE TO RELATED APPLICATION

This application claims priority under 35 U.S.C. § 119(e) to U.S. Provisional Patent Application No. 60/662,190, filed Mar. 16, 2005, which is incorporated herein by reference.

FIELD OF THE INVENTION

The present invention relates generally to analysis of medical imaging data, and, more particularly to a method for expanding the domain of imaging software in a diagnostic work-up.

BACKGROUND OF THE INVENTION

Imaging protocols with modern CT scanners and other imaging equipment now allow for high resolution exam images to be obtained for various parts of the body within short time intervals. The resolution on these routine examinations is now similar in quality to the protocols used for screening or diagnostic protocols used to find specific conditions. In addition, computer-aided detection (CAD) software helps radiologists read medical images such as mammograms and computed tomography (also known as CT or CAT scanning) chest scans.

One example is in the area of coronary artery calcium scoring. Modern scanners allow for evaluation of coronary arteries (calcium in the case of non contrast enhanced scans and the lumen in the case of enhanced scans), even when conducting only a routine CT chest scan. Previously, a specific protocol was required for evaluation of the coronary arteries. Thus, the coronary arteries may now be visualized in a routine chest protocol, such as a CT chest scan obtained to evaluate a lung disease such as pneumonia, with nearly the same quality as in a scan specifically run for finding cardiac related conditions.

With respect to CAD software, computer-aided detection may be used by medical professionals such as radiologists to re-evaluate medical images for a given condition. Typically, a radiologist will review images from a CT scan and then activate CAD software, which marks potential abnormalities for a subsequent review by the radiologist. One example of software useful for a CAD system is disclosed in U.S. Pat. No. 6,766,043 to Zeng, et al., issued Jul. 20, 2004 and entitled "Pleural Nodule Detection from CT Thoracic Images," which is incorporated by reference. Zeng discloses an algorithm that recovers regions of possible pleural nodules left out of an organ field or otherwise undetected due to the nature of low level image processing in the organ field.

Unfortunately, such known methods do not provide an accurate way to detect secondary conditions that may present in a medical image initially acquired for another condition, other than the condition that is the subject of the initial scan. Until now, no systems compensated for the differences in accuracy between an imaging technique directed to a first condition, and a more specific imaging technique directed to testing for a second condition. In contrast, the present invention takes advantage of recent improved image scanning quality to provide, for the first time, a procedure for managing patient care for such secondary conditions while compensating for the differences in accuracy between imaging techniques used for differing tests.

SUMMARY OF THE INVENTION

The present invention provides a method for expanding the domain of imaging software in a diagnostic work-up. The method includes the steps of:

imaging a patient's body parts for a first condition using a first imaging technique directed to a first condition;

acquiring known patient risk factors indicating a second condition;

compensating for differences in accuracy between a first imaging technique directed to a first condition, and a second imaging technique directed to testing for the second condition to generate a set of measures;

placing a range and confidence interval around the set of measures; and evaluating for a second condition using the set of measures and known patient risk factors.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

DESCRIPTION OF THE PREFERRED EMBODIMENTS

Preliminarily, it should be noted that while a particular system and method described in detail herein is for analyzing medical imaging data, such as radiology data, this is not by way of limitation, but solely for the purposes of illustration, and the invention may also be employed for analyzing data of other types. (the clinical information that is used to suggest the risk profile of the patient can come from a variety of sources, i.e. age, smoking history, blood profiles, genetic characterizations etc)

Figure 1:
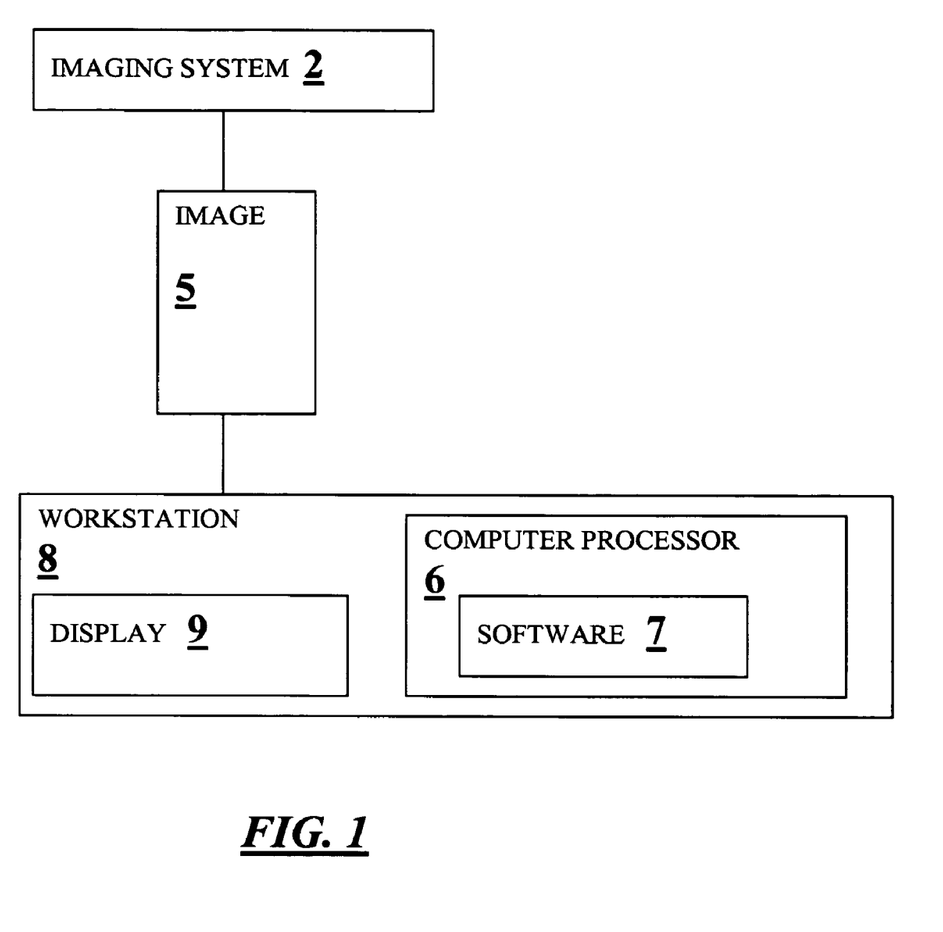
FIG. 1 shows a simplified block diagram of a system for expanding the domain of imaging software in a diagnostic work-up constructed in accordance with one embodiment of the present invention.

Referring now to FIG. 1, there shown is a simplified block diagram of a system for expanding the domain of imaging software in a diagnostic work-up constructed in accordance with one embodiment of the present invention. An imaging system 2 produces image data 5. The image data is processed in a workstation 8. The workstation 8 preferably includes a computer processor 6 running image processing software 7, and a display 9.

The medical imaging system 2 may advantageously include any known medical imaging system. Some useful known imaging systems include computerized tomography scanners, magnetic resonance imagers, positron emission imaging systems, X-ray imaging systems vascular interventional and angiogram/angiography procedures, ultrasound imaging systems and equivalent medical imaging systems.

While there may be some differences in the information acquired, the present invention uses information acquired from, for example, a routine scan and compensates for differences in accuracy of such routine techniques compared with imaging techniques directed to image a specific condition and places a confidence interval and range around the new measures. Thus, patients who undergo, for example, a routine CT chest scan for a first condition or set of conditions, can have their coronaries or other possible secondary conditions evaluated at the same time.

There are several issues regarding measuring the accuracy of a routine scan compared with an image scan for a specific condition. Measurement accuracy and error are treated in our other patent application on measurement error, entitled "MEDICAL IMAGING SYSTEM FOR ACCURATE MEASUREMENT EVALUATION OF CHANGES IN A TARGET LESION," published Nov. 10, 2005 as International Publication No. WO 2005/104943 the entire contents of which are incorporated by reference. Measurement error includes characteristics related to the size of a lesion as well as to the density of the lesion or factors like signal intensity. Estimation of and compensation for such measurement error issues provides more accurate scan results. The estimation and compensation for such measurement errors may be expressed in terms of a confidence interval and range when taking new measures (or other standard statistical measures that are used to characterize degree of accuracy of a measurement).

As detailed in International Publication No. WO 2005/104943 the factors that affect measurement accuracy include primary sources of error like nodule form, scanner parameters, patient factors, algorithm and operator factors. Many of these are interrelated. For example, the definition of the boundary of the nodule will depend upon the nodule tissue, the point spread function of the scanner, patient motion, and other factors. Estimates of error variation are obtained using image models for the error factors and obtaining the parameters for these models from measurements on image phantoms and patients and also by computer simulations. Paired observations of the same patient may be used to reduce error.

Examples of nodule form factors include:
a. Density distribution characteristics, such as
   i. homogeneous or variable distribution characteristics, and/or
   ii. solid tissue or nonsolid or diffuse tissue characteristics.
b. Geometric shape characteristics of the nodule such as
   i. spherical or complex shapes, where complexity may be estimated, for example, as a ratio of surface area to volume normalized to a sphere (=1),
   ii. shapes of multiple components,
   iii. cavities, and/or
   iv. small features close to the reconstruction resolution.
c. Surface characteristics such as whether the nodule is rough (i.e. exhibiting a complex surface) or smooth, where a rough surface implies high average curvature.

Examples of scanner parameters include:
a. Reconstruction resolution further including slice thickness, overlap, and/or in-plane pixel size,
b. X-ray energy (dose): kVp and mAs,
c. Reconstruction filter,
d. Gantry rotation speed,
e. Table speed (pitch),
f. Spatially varying point spread function, and/or
g. Calibration.

Examples of patient factors include the following:
a. Location of the scanned area in the body,
b. Size of the body,
c. Degree of inspiration,
d. Respiration motion (especially at the base of the lungs),
e. Small muscle spasms,
f. Lungs apical region, for example, streaking artifacts, and/or
g. Health of the lung tissue adjacent to the nodule, noting the presence of scars, emphysema, or other health-related conditions.

Operator factors result from operators that assist in the nodule measurement process. For example, an operator may manually modify the estimated nodule boundary resulting in a measurable contribution to the measurement error that can be characterized by observer studies.

Completely automated algorithms typically have situations that are close to intrinsic decision points. For example, an automated algorithm may consider a peripheral bump on a lesion to be an attached vessel or a part of the nodule. Algorithms may be instrumented to indicate how close to decision points they operate and hence factor in the error associated with falling on the other side of the decision point.

Once an image region has been determined to represent a nodule the variance of the measurement may be estimated by considering, for example, the following image model factors.
1. Density: Low variance is associated with homogeneous solid tissue density distribution. High variance is associated with high image noise and low or spatially varying density distribution.
2. Shape: Low variance is associated with a spherical shape form and high variation is associated with a highly irregular shape containing many bumps or cavities.
3. Surface characteristics: At the boundary (edge) of the nodule region low variation is associated with a high image gradient and high variation is associated with low image gradient. Further low variation is associated with a smooth surface while high variation is associated an irregular surface with high curvatures. The boundary region between the nodule and other relatively solid structures such as vessels or the chest wall (where there is little or no image gradient evidence of a boundary) must be treated in a different manner. For low variation these boundary regions should be matched between the two scans in the image segmentation algorithm. Since these regions are less accurately determined than gradient edges, the ratio of non-gradient to gradient edge surface areas is directly related to the variation.
4. Size: In general the larger the nodule, the smaller the proportion of partial voxels the more accurate is the volume estimate. Low variance is associated with large nodules (or very fine scanner resolution) while large variance is usually associated with a smaller nodule (given a similar structural complexity (shape)).

Situations in which the estimated variance may be used include:
A. When two scans are available, all image data and parameters are considered to provide bounds on the estimated growth rate or response to treatment rate.
B. When a single scan is available, the estimated variance is used to determine the minimum time to wait for taking the second scan in order to obtain a clinically significant decision. That is the time to measure a malignant growth rate or a meaningful response within the measurement error bound.

In some situations size will be measured on a two dimensional (2D) area of a single image instead a volume estimated from a set of images.

In one example each step may advantageously be carried out by adaptive software that allows for interaction of a medical professional. The method may further include a step of defining the edge of the at least one target lesion in the imaging data. Edge definition may be determined by applying a threshold and/or a gradient function to the at least one target lesion to determine a boundary for the edge. To further aid diagnosis, the adaptive software applies automatic segmentation and classification techniques as are well known in the art to identify boundaries and segment features, including abnormalities, from body parts, such as lungs that are imaged by the imaging system.

The method of the present invention exploits the fact that the same approach used in screening for work-up and management of findings made is conditional only on the particulars of the radiological findings and the risk profile of the patient. Even though a patient undergoes a CT scan for a first, predetermined condition unrelated to coronary artery disease, for example, the same work-up and management protocol can be used as if he had specifically undergone a scan for cardiac screening. For example, patients that undergo CT chest scans far exceed the number of patients who have heart scans. A screening process according to the method of the invention opens up a much larger patient population for application of coronary artery calcium scoring. As a result, every patient that has a CT scan of the chest can have their coronary arteries assessed at the same time.

Currently, when a radiologist interprets the routine CT scan of the chest, the coronaries are also shown on the scan. While the radiologist may sometimes comment on them, they do not routinely perform scoring on them. The method of the present invention recognizes that there is essentially no difference between a patient who comes for screening and one who has the same risk profile and gets the scan for another condition, and provides a process for scoring such other conditions.

Additional subject information can be made available at the time of imaging, either by data entry prior to a patient undergoing a scan or because the patient is already in the hospital or radiology information system. In this way, when an imaging scan is being performed, the protocol for scanning may advantageously be adapted to provide data for other illnesses indicated by a priori known patient risk factors. Even if the scanning protocol is not so modified, it may advantageously be used with the imaging information that is produced to guide interpretation or reading of the scan results. A reader might be prompted to interpret and score imaging information for another condition, such as, for example, the coronaries because of something in the patient's medical record and knowing the type of scan information begin reviewed.

Taking this a step further, if a medical professional, such as a radiologist or cardiologist, now interprets a scan and only has limited information of the patient, feedback about follow-up procedures may advantageously be provided. If the scan was not directed to a possible secondary condition, and it falls in a certain range of results, the method of the invention may advantageously prompt having the subject return for a scan more appropriately directed to the possible secondary condition, or it might prompt a cardiology consultation or correlation with some other information, including blood tests, or other measures of risk. Whatever standards of risk are currently available may be made available with the imaging results and placed on a workstation so that a limited assessment of risk can be given. As an example, if patient data including height and weight, smoking history and age are known, but not cholesterol characteristics, an estimate of risk can still be made given the patient's imaging findings. A risk estimate can be made even though the scan was not specifically run as a cardiac scan.

In addition to supplying information to the workstation for risk assessment, it is also advantageous in some cases to set-up the scanner itself for acquiring data related to a condition other than the primary condition being scanned. Prior to the method of the present invention, such additional data (i.e. data outside of the field of view for the primary condition being evaluated) was typically discarded. The scanner can be set up for scanning an expanded field of view to acquire imaging data to allow reconstruction of body parts other than body parts presenting a first condition. Patient profile data may also be used to configure a scan in the expanded (or smaller) field of view. For example, if the patient presents a profile showing a substantial risk of breast cancer, the scanner may be preprogrammed or set up to acquire, store and transmit data outside of the field of view used to locate the organ presenting a primary condition as in a CT scan, for example. In this case, imaging data useful for reconstructing the breasts may be added to the data set transmitted to the workstation. With the additional raw data available the operator or a software program may use it to reconstruct a higher resolution image of the breasts than might otherwise be available in the primary filed of view. The additional data may also allow image processing and enhancements such as, for example, re-centering of the image or otherwise modifying the image(s). As in the case of use in a workstation, error ranges may be advantageously used to evaluate images reconstructed from such additional image data as compared to, for example, images from a mammogram that is specifically designed to detect breast lesions.

Another example of extending the method of the invention for learning the risk profile of the patient and applying it to imaging findings when the patient had the exam for another reason uses existing protocols for work-up. The existing protocols come from the screening domain or whatever domain is used for originally generating the information.

For example, currently a work-up for sub 5 mm nodules on baseline screening in a patient being screened for lung cancer is followed up in one year without any ensuing work-up. Using the method of the invention, a similar recommendation can be made for any subject having a scan for a condition other than lung cancer and is found to have a nodule with the same features. Incorporating this information into the reading protocol would be very valuable for many incidentally detected abnormalities. When the scan is being interpreted, the subject's medical record may be checked automatically whenever a particular incidental finding is made so as to incorporate the risk profile into the decision about how to proceed. This is not limited to lung lesions, as incidentally detected lesions are found in every organ.

As a further hypothetical example, a patient may undergo a CT scan of the chest because of asthma. As a result a small incidental nodule may be located in the adrenal gland as may be imaged on the bottom of the scan. In accordance with the method of the present invention, a different management plan is developed than one for a nodule found in a patient having lung cancer or even a history of lung cancer treated in the past. Applying the teachings of the current invention, the imaging findings and their subsequent management are thus made conditional on risk profile of the patient.

Figure 2:
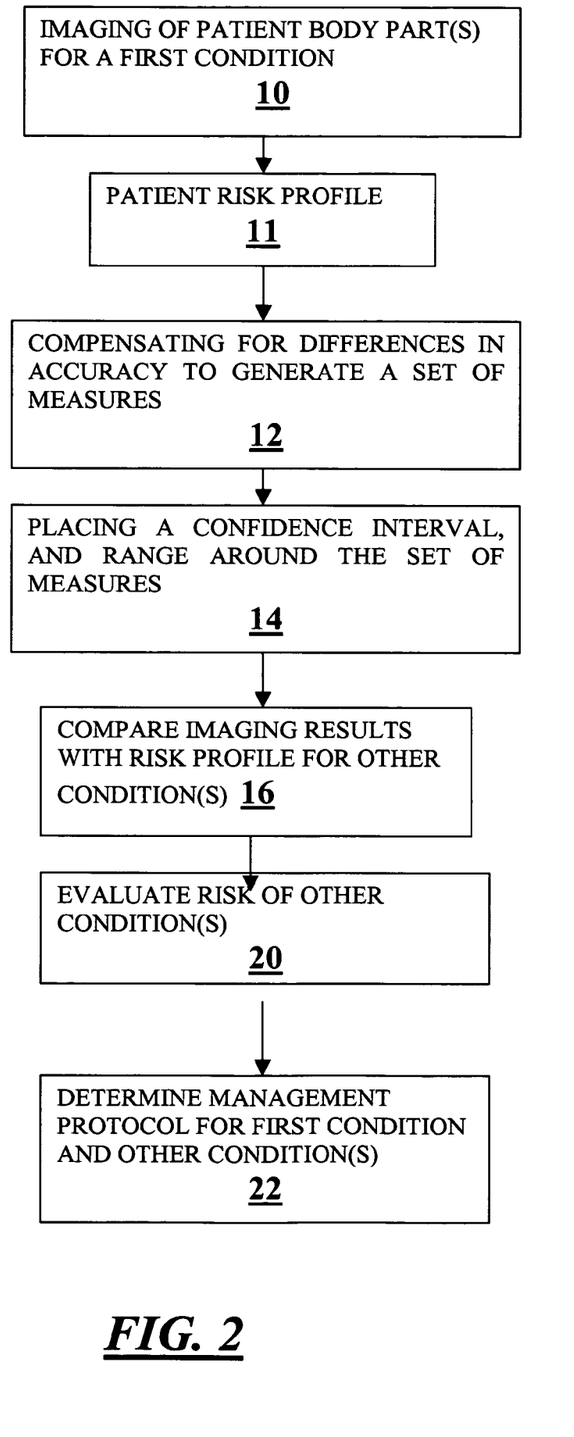
FIG. 2 shows a simplified block diagram of a method for expanding the domain of imaging software in a diagnostic work-up carried out in accordance with one embodiment of the present invention.

Referring now to FIG. 2, a block diagram of a method for expanding the domain of imaging software in a diagnostic work-up is there shown. The method includes the steps of:

imaging a patient's body parts for a first condition using a first imaging technique directed to a first condition at step 10;

acquiring known patient risk factors at step 11;

compensating for differences in accuracy between a first imaging technique directed to a first condition, and a second imaging technique directed to testing for a second condition to generate a set of measures at step 12;

placing a confidence interval and range around the set of measures at step 14; and evaluating for a second condition using the set of measures and known patient risk factors at step 20.

The process may also include determining a management protocol for the first condition and other conditions at step 22. In one useful embodiment the method of the invention may also include prompting to interpret and score imaging information for another condition or conditions and providing feedback for follow-up procedures.

The patient risk profile acquired at step 11 alerts the physician to look for a related secondary condition. Then the related condition may be optimized either on the raw data or on the processed data. Then compensating software at step 12 is used on the secondary condition including compensating for differences. The compensating software also uses the parameters that were used in the primary scan and integrates that information into the compensation.

The steps of compensating for differences in accuracy of imaging techniques at step 12, and placing a confidence interval and range around the set of measures at step 14 may advantageously take into account the scanner parameters detailed above. For example, a first imaging technique used to scan for a first condition will typically have a first reconstruction resolution measurement, while a second imaging technique more appropriate for scanning for a second condition may have a different reconstruction resolution measurement. The reconstruction resolution is generally known from manufacturer's specifications or by calibration. The differences in accuracy of the two types of scan are directly related to the scanner parameters and a set of accuracy measures may be assigned to the first imaging technique based on a relative scale using the second imaging technique as a baseline, for example. A confidence interval and range may advantageously be assigned to the first imaging technique scan based on the set of accuracy measures and other factors using standard statistical algorithms.

Figure 3:
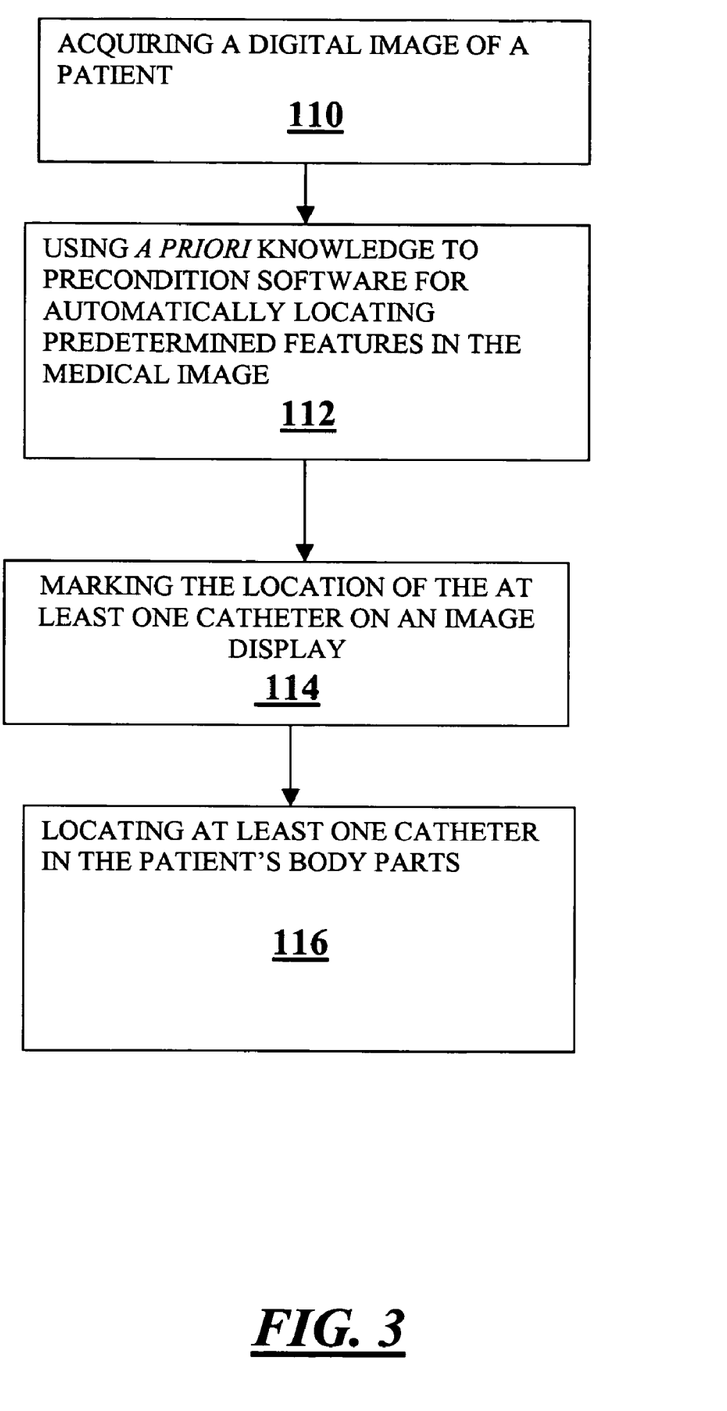
FIG. 3 shows is a flow diagram of a method for locating a catheter in a patient's body carried out in accordance with one embodiment of the present invention.

Referring now to FIG. 3, there shown is a flow diagram of a method for locating a catheter (or other appliance) in a patient's body. The steps include acquiring a digital image of a patient's body parts 110, locating at least one catheter in the patient's body parts 116, and marking the location of the at least one catheter on an image display 114. A further step may optionally include using a priori knowledge to precondition software for automatically locating predetermined features in the medical image related to a catheter or other device 112. The a priori knowledge may include information about the presence of a previously inserted catheter.

Computer aided techniques, including traditional CAD approaches, may be employed to find catheters or tubes that are in the lungs, heart or other parts of the body. Example applications include images produced by plain radiographs and intensive care unit studies or exams. After a medical image is acquired digitally using conventional visioning techniques, various features of any catheters inserted in a patient may be identified using pattern recognition software. Catheter features are well known and include characteristics such as shapes, dimensions and densities. Applying known three dimensional imaging techniques, like CAD techniques, to identify body parts locates the catheters or tubes relative to anatomic sites.

Figure 4:
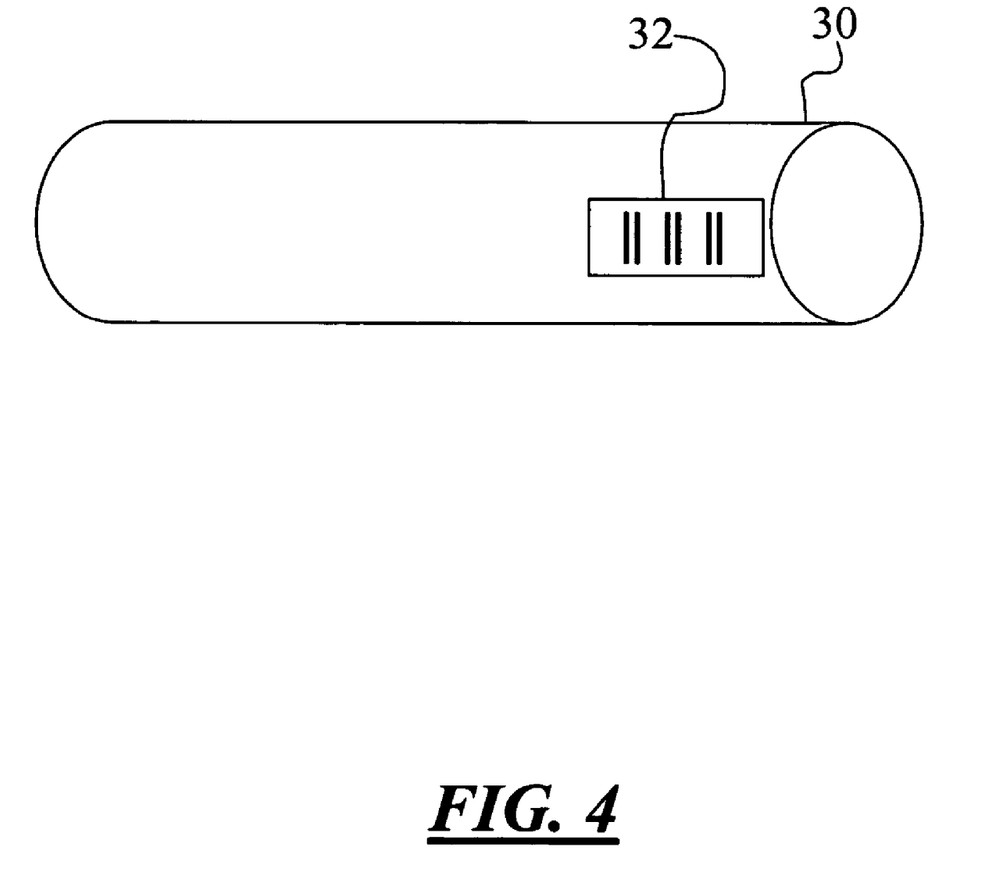
FIG. 4 shows a catheter having a marked catheter tip.

Referring now briefly to FIG. 4, there schematically shown is a catheter having a marked catheter tip. In one example embodiment, a marker 32 may be applied to a catheter tip 30 readily recognizable by pattern recognition software or CAD methods. The marker may be similar to a bar code or other indicia, but can be any marking or indicia visible on a medical image. Since the presence, general location and type of catheter may be a prior known in many cases the software can be preprogrammed with initial conditions to locate a particular marker, or a particular type of problem.

In some cases features on the tubes and catheters themselves that will make them more recognizable. For example, implanting of radiodense material in a tip in a particular pattern that will make the tip more recognizable using pattern recognition software or equivalent techniques. Because catheters can be quite thin, it might be difficult for the radiologist to identify, however the pattern of the radiodense material promotes the ability of an imaging program to recognize it. Such tip markers also enhance the computer software's ability to locate the catheters when they are difficult to recognize either due to technical factors that were not optimally set or due to patient factors such as large size or edema. Such markers will speed up the finding of catheter tips and fewer adjustments of the actual image will be necessary while the radiologist is interpreting the image. Where an inserted catheter includes a tip marker, the method of locating the catheter may further include the step of using a priori knowledge to precondition software for automatically locating a tip marker having at least a selected one of a bar code, indicia, and patterned radiodense material.

For example, the carina of a lung may be located using pattern recognition software and the location of the tip of a marked endotracheal tube. By marking the locations of the endotracheal tube tip relative to the body part on a computer display, an image reader or operator would be aided judging whether the tube is positioned properly.

For example, in the context of intensive care unit (ICU) film, an exam requisition may include information that the patient had a particular catheter inserted or removed. If the presence of a catheter that has a certain appearance (whatever those intrinsic properties are, or have already been described for that device) or its bar code (or other type of marking) is known, locating software can be preconditioned to locate the catheter. Since the catheter type and placement is generally known, the software can more expeditiously identify and locate the catheter even in a noisy or poor image. In such cases the computer software may automatically increase its sensitivity to identify and locate the catheter. In a similar way, if a particular problem is identified before applying the CAD or pattern recognition software program, say a pneumothorax, post procedure, the software can be preconditioned to identify features relating to the known condition more aggressively and with increased sensitivity to its presence.

The invention is not limited to the issue of tubes and catheters and chest X-Rays, but can also be used for other imaging techniques such as CT scan imaging or magnetic resonance imaging (MRI). It is useful to identify devices such as catheters and the like and to locate the tip relative to a preferred location.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. An automated method for expanding the domain of imaging software in a diagnostic work-up, the method comprising the steps of:
    imaging a patient's body parts for a first condition using a first imaging technique directed to a first condition;
    acquiring additional data from the first imaging technique for a second condition by scanning an expanded field of view to reconstruct body parts other than body parts presenting the first condition;
    acquiring known patient risk factors further indicating the second condition;
    compensating for differences in accuracy between the first imaging technique directed to the first condition and a second imaging technique directed to testing for the second condition by using a computer processor to generate a set of measures;
    placing a range and confidence interval around the set of measures using adaptive software; and
    evaluating for a second condition using the set of measures and the known patient risk factors.

2. The method of claim 1 wherein the first imaging technique comprises a CT scan.

3. The method of claim 1 further comprising the step of determining a management protocol for the first condition and other conditions.

4. The method of claim 1 further comprising the step of prompting a user to interpret and score imaging information for another condition.

5. The method of claim 1 further comprising the step of providing feedback for follow-up procedures.

6. The method of claim 1 further comprising the step of locating at least one of a catheter or other appliance in the patient's body parts.

7. The method of claim 6 further comprising the step of marking the location of the at least one catheter on an image display.

8. The method of claim 6 where the at least one catheter includes a tip marker further comprising the step of using a priori knowledge to precondition software for automatically locating predetermined features in the medical image.

9. The method of claim 8 wherein the tip marker comprises at least a selected one of a bar code, indicia, and patterned radiodense material.

10. The method of claim 8 wherein the step of using a priori knowledge includes providing information about the presence of a previously inserted catheter.

11. The method of claim 1 wherein the expanded field of view includes data for reconstruction of a patient's breasts.

12. The method of claim 1 wherein the step of imaging a patient's body parts for a first condition using a first imaging technique covers a first field of view, further comprising the step of reconstructing a second smaller field of view with higher resolution.

13. The method of claim 1 further comprising the step of scanning a smaller field of view to acquire imaging data to allow reconstruction of body parts other than body parts presenting a first condition.

14. The method of claim 1 wherein the additional data is used to reconstruct a higher resolution image of a body part not available in a primary field of view, where the primary field of view covers the first condition.

* * * * *